US000001188H

United States Statutory Invention Registration [19]

[11] Reg. Number: H1188

Nappa et al.

[43] Published: May 4, 1993

[54] PROCESS FOR MAKING 1,1-DICHLORO-1,2-DIFLUOROETHANE

[75] Inventors: Mario J. Nappa, Newark, Del.; Allen C. Sievert, Elkton, Md.

[73] Assignee: E. I. Du Pont de Nemours and Company, Wilmington, Del.

[21] Appl. No.: 587,153

[22] Filed: Sep. 19, 1990

[51] Int. Cl.[5] ..... C07C 17/00

[52] U.S. Cl. ..... 570/169; 570/134; 570/166

[58] Field of Search ..... 570/169

[56] References Cited

U.S. PATENT DOCUMENTS 2,466,189 4/1949 Waalkes ..... 570/169

FOREIGN PATENT DOCUMENTS 1236642 4/1971 United Kingdom .

OTHER PUBLICATIONS

Albert L. Henne & T. Phillip Waalkes, "The Addition of Fluorine to Double Bonds", Oct. 1945, pp. 1639–1640; J. Amer. Chem. Soc. 67.

Rausch et al., "The Addition of Fluorine to Halogenated Olefins by Means of Metal Fluorides", J. Org. Chem. 28, pp. 494–497, Jul. 1962.

Bissell et al., "The Addition of Fluorine to Halogenated Olefins", J. Org. Chem. 29, pp. 1591–1593, Nov. 1963.

*Primary Examiner*—Robert L. Stoll
*Assistant Examiner*—Joseph D. Anthony
*Attorney, Agent, or Firm*—Michael K. Boyer

[57] ABSTRACT

A process for the preparation of 1,1-dichloro-1,2-difluoroethane (HCFC-132c) comprising contacting 1,1-dichloroethylene with lead dioxide and anhydrous hydrogen fluoride. Addition of fluorine to the double bond of vinylidene chloride can be achieved using inexpensive and readily available commercial raw materials.

14 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR MAKING 1,1-DICHLORO-1,2-DIFLUOROETHANE

BACKGROUND OF THE INVENTION

1. Field of the Invention

This invention relates to a process for the preparation of 1,1-dichloro-1,2-difluoroethane (HCFC-132c) from 1,1-dichloroethylene (vinylidene chloride) using a combination of lead dioxide ($PbO_2$) and anhydrous hydrogen fluoride (HF) as fluorinating agent.

2. Description of Related Art 1,1,2-Trichloro-1,2,2-trifluoroethane (CFC-113) has developed a major market as a halogenated solvent and cleaning agent in the electronics, aerospace, and metal working industries. The recent discovery that chlorofluorocarbons (CFCs) contribute to ozone destruction in the upper atmosphere has led to regulations requiring a phase out of its use. This has created a demand for hydrogen-containing chlorofluorocarbon solvents (HCFCs) which have similar properties to CFC-113 but are unstable enough in the atmosphere to largely decompose before reaching the stratosphere. One of these potential replacements is 1,1-dichloro-1,2-difluoroethane (HCFC-132c). The structure of HCFC-132c suggests low toxicity and preliminary tests indicate this compound is an excellent solvent with an appropriate boiling point (48° C.).

One known method for preparing vicinal difluoro compounds is by the addition of fluorine ($F_2$) to the double bond of the corresponding acyclic olefin. While elemental fluorine itself may be used, the high heat of reaction tends to promote undesired side reactions which can result in a reduced yield of the desired $F_2$ addition product. Instead, compounds capable of delivering fluorine, such as high valency metal fluorides, have been used and in certain cases have provided a more controllable reaction. For example, U.S. Pat. No. 2,466,189 discloses the process of adding fluorine to the double bond of a variety of olefins using a mixture of lead dioxide and HF. This work is also reported in an article by Henne and Waalkes (J. Amer. Chem. Soc. 67, 1639–1640 (1945)) in which it is surmised that the lead dioxide and HF function by generating nascent lead tetrafluoride, which decomposes into lead difluoride and $F_2$ to be accepted by the olefin. The reaction was generally carried out by adding the olefin to the lead dioxide, cooling the mixture to −20° C. or below, adding the HF, allowing the temperature to rise to 80° C. to 100° C., and separating the resulting material. The importance of the exact procedure for preparing the lead tetrafluoride was illustrated by experiments in which the lead dioxide was added after the olefin and HF were mixed. In this case no fluorination occurred. The Henne work was primarily focused on fully halogenated compounds. When this procedure was applied to 1,2-dichloroethylene, the yield of the addition product 1,2-dichloro-1,2 difluoroethane was the poorest of all those reported, only 17% of theory. It was not tried on the fluorination of 1,1-dichloroethylene, nor was this important and well-known olefin listed among the olefins representative of those to which the process could be applied.

Rausch et al. (J. Org. Chem. 28, 494 (1963)) extended the above work to other metal fluorides such as cobalt trifluoride, manganese trifluoride, silver difluoride, and cerium tetrafluoride. In an experiment to fluorinate 1,2-dichloroethylene with cobalt trifluoride at a reaction temperature of about 35° C., the yield of 1,2-dichloro-1,2-difluoroethane was 53% of theory compared to the yield of 17% with lead tetrafluoride. In a similar experiment using cobalt trifluoride to fluorinate 1,1-difluoroethylene at a reaction temperature of 125° C., the yield of 1,1,1,2-tetrafluoroethane ranged from 54% to 81% of theory. Nearly all the olefins tested gave at least some of the desired addition product. Surprisingly, when the same experiment was repeated on 1,1-dichloroethylene at a reaction temperature of 35° C., they found none of the desired addition product. Instead a variety of products were found, all of which were partially dehydrohalogenated. The authors concluded, "The failure of 1,1-dichloroethylene to produce the addition compound may be attributed to its lack of stability."

In view of the above and not withstanding the presence of a catch-all phrase in the Waalkes patent that other acyclic olefinic compounds may be employed, the data presented in this patent and corresponding publication by Henne et al. cited in the patent establishes that for the series of perchloroethylene, trichloroethylene, and 1,2-dichloroethylene diminishing yields of symmetric addition of fluorine across the double bond is observed. Furthermore, Henne et al. admits that addition of fluorine to the double bond has been observed in only a few cases and is very impractical because of the large amount of heat evolved breaks down the organic material. The above in combination with the observation by Rausch et al. that fluorinating 1,2-dichloroethylene using $CoF_3$ or $PbF_4$ to produces symmetric addition and when 1,1-dichloroethylene was fluorinated no symmetric addition occurred but instead dehydrohalogenation occurred exclusively leads one skilled in the art to conclude that 1,1-dichloroethylene will not under go symmetric addition of fluorine but will dehydrohalogenate.

The first successful attempt to produce HCFC-132c was a laboratory preparation reported by Bissell and Fields (J. Org. Chem. 29, 1591 (1964)). They used a mixture of lead dioxide and sulfur tetrafluoride ($SF_4$) in a 25 ml reactor to add fluorine to the double bond of a variety of halogenated olefins including 1,1-dichloroethylene. In a single run, they reported a yield of 1,1-dichloro-1,2-difluoroethane of 59% of theory, with a reaction temperature varying from below 0° C. to 100° C. in the course of the reaction. In a broader set of experiments on the fluorination of trichloroethylene, they concluded that preformed lead tetrafluoride gave very low yields and conversions. This indicates that the above results with $SF_4$ and $PbO_2$ cannot be extrapolated to $PbF_4$ made by other means. However, $SF_4$ is a highly toxic material with inhalation toxicity comparable to phosgene. In addition it is a very expensive chemical costing about 50 times as much as the HF and it is available only in small high pressure cylinders. Thus, $SF_4$ is used primarily as a laboratory reagent, with very limited commercial applications and is not presently considered to be a practical means of preparing HCFC-132c. Consequently none of the above references teach a process suitable for preparing 1,1-dichloro-1,2-difluoroethane which could be used with low-priced commercial raw materials.

SUMMARY OF THE INVENTION

According to the present invention, a process for preparing 1,1-dichloro-1,2-difluoroethane is provided comprising the steps of:

(a) contacting 1,1-dichloroethylene with lead dioxide and anhydrous hydrogen fluoride at an effective temperature and for a sufficient time to convert at least a portion of the 1,1-dichloroethylene to 1,1-dichloro-1,2-difluoroethane; and (b) recovering the 1,1-dichloro-1,2-difluoroethane substantially free of dehydrohalogenated products.

The process according to the present invention further involves contacting the 1,1-dichloroethylene, HF and lead dioxide at a temperature of about −60° C. to about 0° C. and then raising the temperature or allowing it to rise to a temperature at which the reaction proceeds vigorously, i.e., to a temperature of about 0° C. up to about 90° C. After holding the reaction mixture at the high temperature to optimize and/or drive the reaction toward completion, the organic phase can then be isolated and the desired 1,1-dichloro-1,2-difluoroethane be recovered substantially free of dehydrohalogenated products. For purposes of this invention, substantially free of dehydrohalogenated products means that virtually no halogen for hydrogen exchange reaction is detectable as exemplified later.

It is an object of the present invention to provide a method of adding fluorine to the double bond of vinylidene chloride such as to produce HCFC-132c. It is a further object of the present invention to provide such a process using inexpensive and readily available commercial raw materials. Fulfillment of these objects and the presence and fulfillment of additional objects will be apparent upon complete reading of the specification and attached claims.

PREFERRED EMBODIMENTS

This invention involves, for example but not by way of limitation, the addition of 1,1-dichloroethylene and anhydrous HF in either order to particulate or granular lead dioxide ($PbO_2$) at a temperature of about −60° C. to about 0° C., and allowing the temperature to rise to a point where the reaction proceeds vigorously, holding at a temperature between 0° C. and 80° C. until the reaction is complete, separating the organics and unused HF from the lead compounds, and purifying the organics to recover 1,1-dichloro-1,2-difluoroethane (HCFC-132C). Good contact between the solids and liquids in the reaction mass is required and can be achieved by agitation, as by stirring, shaking, or recirculation of fluids. Inadequate agitation of the thick and heavy reaction mass will lead to poor yields of the desired product. The 1,1-dichloroethylene should be mixed with lead dioxide in the proportion of at least 0.5 mole of the olefin for each mole of $PbO_2$. Generally there will be from about 0.1 to about 4 moles of the olefin per mole of $PbO_2$, preferably about 0.5-2 moles of olefin per mole of $PbO_2$, and most preferably about 1 mole of olefin per mole of $PbO_2$. Large excesses or deficiencies of the olefin may be used, but without advantage. The HF will generally be used in the proportion of at least 3 moles per mole of lead dioxide. Proportions of from about 3 to about 35 moles of HF per mole of $PbO_2$ have been employed with satisfactory results. Preferably about 5 to 20 moles of HF per mole of $PbO_2$ will be used.

It has also been found that addition of a fluoride salt has a beneficial effect on the yield of HCFC-132c by reducing the amount of by-products formed. Suitable fluoride salts for the process of the invention include MF (M=Li, Na, K, Cs), $(NH_4)HF_2$, or $NR_{4-x}H_xF$ where x=1 to 4 and R=$C_1$ to $C_{12}$ alkyl. The preferred fluoride salts are LiF, NaF, KF, CsF, and $NH_4F$. Preferably the fluoride salt is added to the reactor along with $PbO_2$ and 1,1-dichloroethylene. Generally about 0 to 2 moles of fluoride salt can be added per mole of $PbO_2$, preferably about 0.5 to 1.5 moles per mole.

The overall reaction according to the present invention is exothermic, but is quite slow at temperatures below 0° C. In the absence of cooling sufficient to remove the heat as fast as it is generated, the mixture will slowly warm up with acceleration of the reaction until, at a temperature above 0° C. the reaction becomes quite vigorous, generating large amounts of heat. The temperature at which the vigorous exothermic reaction takes place will depend to some degree on the size and shape of the charge and reaction vessel. Generally such temperature is between −25° C. and 0° C. We have found that in order to successfully carry out the reaction with the production of substantial yields of the desired HCFC-132c, the $PbO_2$, 1,1-dichloroethylene, and HF should be mixed together in the desired proportions at a temperature of about 0° C. or below, and the reaction carried out in a closed reaction vessel. Preferably the reactants are mixed together at a temperature of below 0° C., and most preferably from about −25° C. to about −40° C. For convenience, the lead dioxide is usually placed in the reaction vessel first. The vessel is then sealed and evacuated. Weighed portions of 1,1-dichloroethylene and the HF are then added from cylinders. The order of addition of 1,1-dichloroethylene and HF may be varied. Cooling is generally applied to the reactor during the addition of 1,1-dichloroethylene or HF to the reactor. It is advantageous to hold the reaction at a low temperature, preferably 0° C. or below, while the contents of the reactor are being mixed. After the reactants have been mixed and held at an initial low temperature for a desired period of time, the reaction temperature is allowed to rise above 0° C. This may be accomplished by removing the cooling from the vessel and allowing the heat of reaction to raise the temperature or by applying heat to the vessel. Due to the heat of reaction, the temperature of the mixture at the end of the vigorous reaction will usually be much higher than that at which the vigorous reaction starts. It will usually be desirable to maintain the mixture at the elevated temperature for a substantial period of time so as to complete the reaction. However, too high a temperature will cause a decrease in yield of the desired HCFC-132c due to various side reactions. We have found it desirable, after the vigorous reaction has subsided, to keep the mixture at a temperature of 0° C. to 80° C., preferably 0° C. to 40° C., for a suitable period of time to insure completeness of the reaction without loss of the product to side reactions. The amount of time required to hold the reaction at the mixing stage and at the final reaction temperature will depend to a large degree on the configuration of the reactor and the degree of mixing attainable; however, hold times of 5 minutes to 5 hours are generally adequate.

Pressure is not critical for this process; however, because of the vigor of the reaction, it should be carried out in a vessel able to withstand the pressures generated should the reactants overheat for any reason. The reaction is conveniently, and preferably, carried out under sufficient pressure to keep the organics and HF in a liquid state to promote adequate mixing and reaction with the lead dioxide. These reaction pressures are readily achieved by employing a sealed reactor or one equipped with a controllable pressure relief valve.

The reaction vessel will usually be provided with means for agitation, heating and cooling, and with a reflux column. The vessel should be constructed from materials which are resistant to the corrosive effects of HF and fluorine such as "HASTELLOY" and "INCONEL".

The raw materials used for this process may be the usual commercial grades of 1,1-dichloroethylene, anhydrous HF, and particulate or granular lead dioxide. The by-product lead difluoride from this reaction may optionally be used for purification and sale as lead difluoride, fluorinated to lead tetrafluoride for sale, or used for recovery of lead value. The organic by-products may be optionally recycled, isolated for other uses or, if no uses are developed, disposed of by incineration or other means in a permitted facility.

The following examples are presented to further illustrate specific embodiments of the present invention.

EXAMPLE 1

A 150 ml stainless steel cylinder containing a small polytetrafluoroethylene-coated magnetic stirring bar was charged with 9.4 g (0.097 mole) of 1,1-dichloroethylene and 23.3 g (0.097 mole) of powdered reagent grade lead dioxide. The reactor and contents were cooled with liquid nitrogen (−196° C.). The vapor space was then evacuated under high vacuum and 23.4 g (1.17 mole) of anhydrous HF was vacuum distilled onto the frozen mix of 1,1-dichloroethylene and lead dioxide. The cylinder was then warmed to 0° C. and stirred for 1 hour. The temperature was then raised to 25° C. and the mixture stirred for an additional hour. The reaction was quenched by immersing the cylinder in liquid nitrogen. The cylinder was evacuated and the volatile components distilled out of the reactor and subsequently drowned in 75 g of ice. The organic layer was then separated from the aqueous layer and washed with a 5 weight % solution of sodium bicarbonate followed by a water wash and drying over sodium sulfate. The isolated organic material weighed 9.28 g and analyzed as 39% 1,1-dichloroethylene by gas chromatography (GC). Based on the amount of 1,1-dichloroethylene consumed, the yield of the desired product, HCFC-132c, was 28% of theory.

EXAMPLES 2-8

Using the same type of equipment and procedure of Example No. 1, seven additional runs were performed involving the addition of fluorine to 1,1-dichloroethylene. The relative molar amount of each ingredient, the reaction temperatures, and hold times were varied and are presented in Table I. In the examples where a fluoride salt was added (i.e., 5, 6 and 7), the salt was added along with the 1,1-dichloroethylene and lead dioxide, prior to the addition of HF. The resulting weight of organic product, its composition by GC, and the calculated percent yield of HCFC-132c based on 1,1-dichloroethylene consumed are also shown. Example 1 is included in Table I for comparison. The following is the key to abbreviations used in Tables I and II:

| | |
|---|---|
| DCE | 1,1-dichloroethylene |
| HCFC-130a | 1,1,1,2-tetrachloroethane |
| HCFC-131a | 1,1,2-trichloro-1-fluoroethane |
| HCFC-132b | 1,2-dichloro-1,1-difluoroethane |
| HCFC-132c | 1,1-dichloro-1,2-difluoroethane |
| HCFC-141b | 1,1-dichloro-1-fluoroethane |
| HCFC-142b | 1-chloro-1,1-difluoroethane |
| HCFC-352kff* | 1,1,4,4-tetrachloro-1,4-difluorobutane |
| MF | fluoride salt (M = Li, Na, K, or $NH_4$) |

*New HCFC solvent as confirmed by NMR; b.p. 165° C.

TABLE I

| | Example No. | | | | | | | |
|---|---|---|---|---|---|---|---|---|
| | 1 | 2 | 3 | 4 | 5 | 6 | 7 | 8 |
| Mole Ratio | | | | | | | | |
| DCE | 1 | 1 | 3 | 1 | 1 | 1 | 1 | 1.2 |
| $PbO_2$ | 1 | 1 | 1 | 3 | 1 | 1 | 1 | 1 |
| HF | 12 | 8 | 36 | 24 | 12 | 12 | 20 | 9 |
| MF | 0 | 0 | 0 | 0 | 0.5 (NaF) | 1 ($NH_4F$) | 1 (KF) | 0 |
| Initial Temp, °C. | 0 | 0 | 0 | 0 | 0 | 0 | 0 | 50 |
| Hold Time, h | 1 | 1 | 5 | 5 | 1 | 1 | 1 | 2 |
| Final Temp. °C. | 25 | 25 | 0 | 0 | 25 | 25 | 25 | 50 |
| Hold Time, h | 2 | 1 | — | — | 2 | 1 | 2.5 | — |
| DCE Charged, g | 9.5 | 16.1 | 4.0 | 4.0 | 9.7 | 8.9 | 8.1 | 12.0 |
| Organic product recovered, g | 9.3 | 12.0 | 2.1 | 2.4 | 6.0 | 2.8 | 2.3 | 11.6 |
| Yield HCFC-132c, % | 27 | 14 | 13 | 14 | 32 | 19 | 11 | 17 |
| | Organic Analysis, GC Area % | | | | | | | |
| Component DCE | 0.5 | 55.0 | 17.1 | 14.7 | 49.1 | 12.2 | 12.2 | 16.0 |
| HCFC-130a | 0.4 | 0 | 0.6 | 0.6 | 0.9 | 0 | 0 | 1.4 |
| HCFC-131a | 21.6 | 2.7 | 12.4 | 13.3 | 8.9 | 3.9 | 15.4 | 20.9 |
| HCFC-132b | 0 | 0 | 0 | 0 | 0.1 | 0.1 | 2.9 | 0 |
| HCFC-132c | 38.7 | 11.6 | 28.6 | 27.9 | 36.8 | 74.5 | 47.4 | 20.8 |
| HCFC-141b | 0.2 | 26.0 | 23.7 | 18.3 | 2.4 | 1.4 | 13.3 | 21.5 |
| HCFC-142b | 2.8 | 0.4 | 1.3 | 0.7 | 0.1 | 0 | 0.4 | 3.5 |
| HCFC-352kff | 32.2 | 2.2 | 14.0 | 22.4 | 15.3 | 6.0 | 6.4 | 8.6 |

EXAMPLE 9

A 2L "HASTELLOY" C autoclave equipped with mechanical agitation, resistance heating, and inner cooling coils was charged with 480 g (2 mole) of lead dioxide. The autoclave was then sealed, −40° C. cooling applied to the coils, and 194 g (2 mole) of 1,1-dichloroethylene were added. The agitation was then started and 720 g (3 mole) of anhydrous HF was added gradually. After a brief exotherm, the temperature of the reaction stabilized at −35° C. and was held for 0.9 hour. The reactor was then warmed to 26° C. and held for 0.7 hour. The volatile products including HF were distilled into a liquid nitrogen-cooled receiver and the distillate quenched in ice. The recovered organic layer was then weighed and analyzed by GC. Based on the amount of 1,1-dichloroethylene consumed, the yield of the desired product was 35%.

EXAMPLES 10–13

In Example 10 and 11, the same type of equipment and procedure was used as in Example 9. In Examples 12 and 13, the procedure was changed by adding the HF prior to the 1,1-dichloroethylene. The relative molar amount of each ingredient, the reaction temperatures, and hold times were varied as shown in Table II. In Example 12, $NH_4F$ was added to the reactor with $PbO_2$.

TABLE II

| | Example No. | | | | |
|---|---|---|---|---|---|
| | 9 | 10 | 11 | 12 | 13 |
| Mole Ratio | | | | | |
| DCE | 1 | 1 | 1 | 1 | 1 |
| $PbO_2$ | 1 | 1 | 1 | 1 | 1 |
| HF | 12 | 12 | 12 | 12 | 12 |
| MF | 0 | 0 | 1 ($NH_4F$) | 0 | 0 |
| Initial Temp. °C. | −35 | −5 | 0 | −33 | −39 |
| Hold Time, h | 0.9 | 1.0 | 1.2 | 1.3 | 1.0 |
| Final Temp. °C. | 26 | 21 | 25 | 26 | 23 |
| Hold Time, h | 0.7 | 1.0 | 1.2 | 1.0 | 0.6 |
| DCE Charged, g | 291 | 194 | 194 | 291 | 291 |
| Organic Product Recovered, g | 244 | 189 | 178 | 263 | 222 |
| Yield HCFC-132c, % | 35 | 15 | 39 | 44 | 30 |
| Organic Analysis, GC Area % Component | | | | | |
| DCE | 9.9 | 0.4 | 70.7 | 3.6 | 0.1 |
| HCFC-131a | 6.7 | 7.4 | 1.3 | 7.9 | 5.6 |
| HCFC-132b | 0 | 0.05 | 0.09 | 0.002 | 0 |
| HCFC-132c | 52.4 | 20.7 | 17.2 | 64.6 | 53.9 |
| HCFC-141b | 17.7 | 39.8 | 4.9 | 9.1 | 25.7 |
| HCFC-142b | 0.3 | 1.1 | 0.2 | 0.1 | 0.3 |
| HCFC-352kff | 11.5 | 27.4 | 3.1 | 12.7 | 13.6 |

Having thus described and exemplified the invention with a certain degree of particularity, it is to be understood that such details are solely for the purpose of illustration, and that many variations can be made without departing from the spirit and scope of the invention. Thus the following claims are not to be interpreted as being unduly limited, but are to be afforded a scope commensurate with the wording of each element of the claims and equivalents thereto.

We claim:

1. A process for preparing 1,1-dichloro-1,2-difluoroethane comprising the steps of:

(a) contacting 1,1-dichloroethylene with lead dioxide and anhydrous hydrogen fluoride at an effective temperature and for a sufficient time to convert at least a portion of said 1,1-dichloroethylene to 1,1-dichloro-1,2-difluoroethane substantially free of dehydrohalogenation; and (b) recovering said 1,1-dichloro-1,2-difluoroethane substantially free of dehydrohalogenated products.

2. A process of claim 1 wherein said contacting of 1,1-dichloroethane with lead dioxide and anhydrous hydrogen fluoride is initially performed at about −60° C. to about 0° C. with mixing followed by raising the temperature above 0° C. up to about 80° C. to promote vigorous reaction.

3. A process of claim 1 wherein said anhydrous hydrogen fluoride is initially mixed with said lead dioxide followed by addition of said 1,1-dichloroethylene.

4. A process of claim 2 wherein said anhydrous hydrogen fluoride is initially mixed with said lead dioxide followed by addition of said 1,1-dichloroethylene.

5. A process of claim 1 wherein said 1,1-dichloroethylene is initially mixed with said lead dioxide followed by addition of said anhydrous hydrogen fluoride.

6. A process of claim 2 wherein said 1,1-dichloroethylene is initially mixed with said lead dioxide followed by addition of said anhydrous hydrogen fluoride.

7. A process of claim 1 wherein said contacting of 1,1-dichloroethylene with lead dioxide and anhydrous hydrogen fluoride is in the presence of an effective amount of a fluoride salt to enhance the conversion to 1,1-dichloro-1,2-difluoroethane.

8. A process of claim 7 wherein said fluoride salt is selected from the group consisting of LiF, NaF, KF, $(NH_4)HF_2$ and $NR_{4-x}H_xF$ where $x=1$ to 4 and R is a $C_1$ to $C_{12}$ alkyl.

9. A process of any one of claims 1 through 6 wherein the mole ratio of 1,1-dichloroethylene to lead dioxide is about 0.5 to about 4.

10. A process of claim 8 wherein the mole ratio of 1,1-dichloroethylene to lead dioxide is about 0.5 to about 4.

11. A process of claims 1 through 6 wherein the mole ratio of said hydrogen fluoride to said lead dioxide is about 5 to about 20.

12. A process of claim 8 wherein the mole ratio of said hydrogen fluoride to said lead dioxide is about 5 to about 20.

13. A process of claim 8 wherein the mole ratio of said fluoride salt to said lead dioxide is up to about 2.

14. A process of claim 9 wherein the mole ratio of said fluoride salt to said lead dioxide is up to about 2.

* * * * *